(12) United States Patent
Hubbard, Jr.

(10) Patent No.: US 6,840,117 B2
(45) Date of Patent: *Jan. 11, 2005

(54) PATIENT MONITORING SYSTEM EMPLOYING ARRAY OF FORCE SENSORS ON A BEDSHEET OR SIMILAR SUBSTRATE

(75) Inventor: James E. Hubbard, Jr., Derry, NH (US)

(73) Assignee: The Trustees of Boston University, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/378,340

(22) Filed: Mar. 3, 2003

(65) Prior Publication Data

US 2003/0136201 A1 Jul. 24, 2003

Related U.S. Application Data

(60) Continuation of application No. 09/791,114, filed on Feb. 22, 2001, now Pat. No. 6,546,813, which is a continuation-in-part of application No. 09/169,759, filed on Oct. 9, 1998, now Pat. No. 6,223,606, which is a division of application No. 08/780,435, filed on Jan. 8, 1997, now Pat. No. 5,821,633.

(51) Int. Cl.[7] ............................................... G01D 7/00
(52) U.S. Cl. .............................................. 73/862.041
(58) Field of Search .................... 73/862.041, 862.042, 73/862.043, 862.044, 862.045, 862.046

(56) References Cited

U.S. PATENT DOCUMENTS

| | | | |
|---|---|---|---|
| 3,599,199 A | 8/1971 | Bunting | 340/286 |
| 4,135,241 A | 1/1979 | Stanis et al. | 364/200 |
| 4,583,084 A | 4/1986 | Henderson et al. | 340/573 |
| 4,739,299 A | 4/1988 | Eventoff et al. | 338/99 |
| 4,810,992 A | 3/1989 | Eventoff | 338/99 |
| 4,963,702 A | 10/1990 | Yaniger et al. | 178/18 |
| 5,010,772 A | 4/1991 | Bourland et al. | 73/862.04 |

(List continued on next page.)

FOREIGN PATENT DOCUMENTS

| | | |
|---|---|---|
| EP | 0 222 640 A2 | 5/1987 |
| GB | 2 197 121 A | 5/1988 |

OTHER PUBLICATIONS

Interlink Electronics, Inc. "Force and Position Sensing Resistors".
IEE Automotive USA, "Force Sensing Resistor Technology".

(List continued on next page.)

*Primary Examiner*—Max Noori
(74) *Attorney, Agent, or Firm*—Weingarten, Schurgin, Gagnebin & Lebovici LLP (57) ABSTRACT

A patient monitoring system includes a replaceable laminar sensor to be placed on a bed, the sensor including distributed force sensing elements providing output signals to processing apparatus including a near-bed processor and a central processor coupled to the near-bed processor by a wireless communication link. The processing apparatus applies spatial weighting to the sensor output signals to derive the force distribution across the sensor, and processes the force distribution over time to generate patient status information such as patient presence, position, agitation, seizure activity, respiration, and security. This information can be displayed at a central monitoring station, provided to a paging system to alert attending medical personnel, and used to update medical databases. The sensor may be manufactured from layers of olefin film and conductive ink to form capacitive sensing elements.

18 Claims, 9 Drawing Sheets

U.S. PATENT DOCUMENTS

| | | | |
|---|---|---|---|
| 5,158,091 A | 10/1992 | Butterfield et al. | 128/672 |
| 5,209,126 A | 5/1993 | Grahn | 73/862.046 |
| 5,273,046 A | 12/1993 | Butterfield et al. | 128/672 |
| 5,375,397 A * | 12/1994 | Ferrand et al. | 54/66 |
| 5,400,662 A | 3/1995 | Tamori | 73/862.046 |
| 5,503,029 A | 4/1996 | Tamori | 73/862.046 |
| 5,561,412 A | 10/1996 | Novak et al. | 340/286.07 |
| 5,571,973 A | 11/1996 | Taylot | 73/862.046 |
| 5,678,448 A | 10/1997 | Fullen et al. | 73/172 |
| 5,699,038 A | 12/1997 | Ulrich et al. | 340/286.07 |
| 5,821,633 A * | 10/1998 | Burke et al. | 307/10.1 |
| 5,844,488 A | 12/1998 | Musick | 340/573 |
| 5,908,027 A | 6/1999 | Butterfield et al. | 128/627 |
| 6,147,592 A | 11/2000 | Ulrich et al. | 340/286.07 |
| 6,216,545 B1 | 4/2001 | Taylor | 73/862.042 |
| 6,223,606 B1 * | 5/2001 | Burke et al. | 73/862.041 |
| 6,292,102 B1 | 9/2001 | Smith | 340/604 |
| 6,297,738 B1 | 10/2001 | Newham | 340/573.1 |
| 6,307,476 B1 | 10/2001 | Smith et al. | 340/573.1 |
| 6,417,777 B2 | 7/2002 | Fitzgerald et al. | 340/687 |
| 6,546,813 B2 * | 4/2003 | Hubbard, Jr. | 73/862.041 |
| 2002/0103674 A1 | 8/2002 | Reeder et al. | 705/3 |

OTHER PUBLICATIONS

Rn+, "Fall Prevention Systems Product Information", Date Unknown.

Curbell Product Information, http://www.curbell.com, Jan. 23, 2000.

Occupancy Monitoring System Information, Jul. 30, 1999.

Global DME Fall Reduction System, Jul. 30, 1999.

Micro–Tech Medical Care Mate Product Information, Jul. 30, 1999.

Fall Care Product Information, Jul. 30, 1999.

Bed–Check Corporation Product Information, Jul. 30, 1999.

* cited by examiner

PATIENT MONITORING SYSTEM EMPLOYING ARRAY OF FORCE SENSORS ON A BEDSHEET OR SIMILAR SUBSTRATE

CROSS REFERENCE TO RELATED APPLICATIONS

This application is a continuation of U.S. patent application Ser. No. 09/791,114 filed Feb. 22, 2001, now U.S. Pat. No. 6,546,813; which is a continuation in part of U.S. patent application Ser. No. 09/169,759 filed Oct. 9, 1998, which issued May 1, 2001 as U.S. Pat. No. 6,223,606; which is a divisional of U.S. patent application Ser. No. 08/780,435 filed Jan. 8, 1997, which issued on Oct. 13, 1998 as U.S. Pat. No. 5,821,633.

STATEMENT REGARDING FEDERALLY SPONSORED RESEARCH OR DEVELOPMENT

Not Applicable

BACKGROUND OF THE INVENTION

The present invention is related to the field of patient monitoring equipment.

Patient monitoring systems are used in many settings to assist medical personnel in providing care. In many settings, such as hospital wards and nursing homes, there can be problems associated with patients' getting out of bed without supervision or assistance. A patient may suffer a fall whose effects can range from minor to major. Older patients are at risk of breaking their hips in a fall, requiring extended bed rest and attendant problems. Systems have been known that monitor whether a patient is present in a bed or wheelchair. Essentially, these systems employ a flat sensor laid on the mattress or cushion, and electronic apparatus that responds to signals from the sensor. For example, the strength of a sensor output signal may be proportional to the weight applied to the sensor. The electronic apparatus therefore compares the sensor output signal with one or more predetermined values corresponding to significant thresholds of interest. For example, if the sensor output signal falls below a predetermined low value, the apparatus generates an indication that the patient has gotten out of bed.

Prior patient monitoring systems have used sensors having certain drawbacks that limit performance. One such drawback is size. Sensors to be used on a bed are as wide as the bed, but extend only about a foot in the longitudinal direction. These sensors are intended for placement in the middle of the bed, on the assumption that a patient's weight is concentrated there. However, a patient may move into a position away from the sensor, resulting in a false alarm. Existing sensors have also employed switches as sensing elements, which can provide only a binary indication. Due to the lack of resolution, only limited information can be obtained from the sensor.

BRIEF SUMMARY OF THE INVENTION

In accordance with the present invention, a sensor-based patient monitoring system is disclosed incorporating features that overcome limitations of the prior art. In addition to having superior performance for traditional uses, such as reducing the incidence of patient falls, the system can be used for a variety of other clinical purposes to assist medical personnel and enhance the quality of care.

The system includes a replaceable laminar sensor placed on a bed or similar surface, the sensor including distributed force sensing elements providing output signals to processing apparatus for processing the force distribution information. The processing apparatus includes a near-bed processor and a central processor coupled to the near-bed processor by a wireless communication link. The processing apparatus applies spatial weighting to the sensor output signals to derive the force distribution across the sensor, and processes the force distribution information over time to generate pertinent patient status information. The information can vary depending on the operational purpose for the monitoring. For example, the information can include patient presence, position, agitation, seizure activity, or respiration. The information can be used to generate a display at a central monitoring station, and to update medical databases coupled to the central processor. The information can also be provided to a paging system to alert attending medical personnel.

The disclosed laminar sensor is made of layers of olefin film having patterns of conductive ink deposited thereon to form capacitive sensing elements, ground planes, and signal traces. The layers are laminated with a foam core selected to provide desired sensitivity of the capacitive sensing elements for a range of expected patient weights. Both a low-cost process and a high-volume process for manufacturing the sensor are shown.

Other aspects, features, and advantages of the present invention are disclosed in the detailed description that follows.

BRIEF DESCRIPTION OF THE SEVERAL VIEWS OF THE DRAWING

The invention is more fully understood by reference to the following Detailed Description in conjunction with the Drawing, of which:

FIG. 9 (consisting of FIGS. 9a and 9b) is a flow diagram of a single-station process of manufacturing the sensing sheet of FIG. 2;

FIG. 11 (consisting of FIGS. 11a and 11b) is a flow diagram of a multiple-station process of manufacturing the sensing sheet of FIG. 2.

DETAILED DESCRIPTION OF THE INVENTION

The disclosure of U.S. patent application Ser. No. 09/169,759, filed Oct. 9, 1998 and entitled Center Of Weight Sensor, is hereby incorporated by reference herein.

Figure 1:
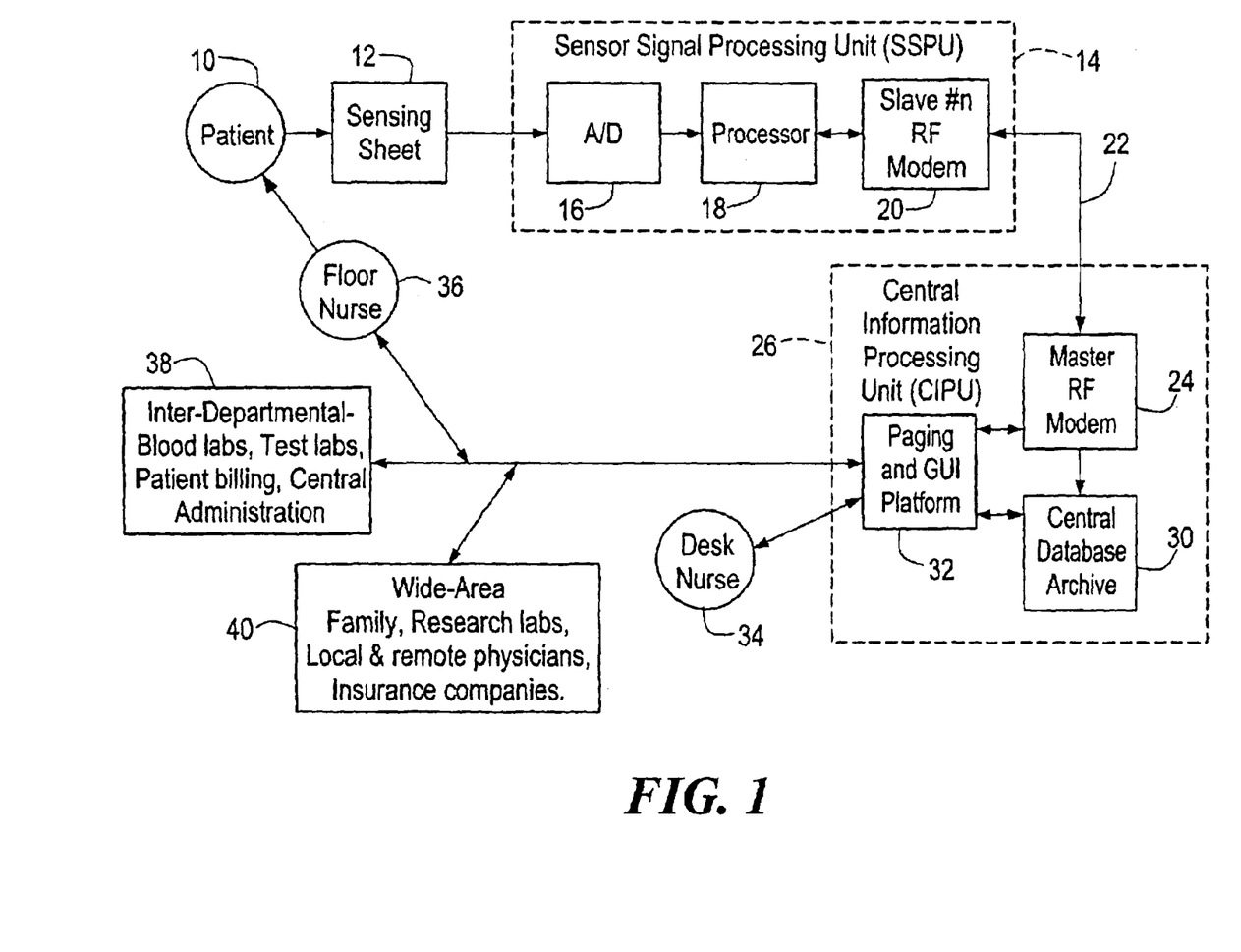
FIG. 1 is a block diagram of a patient monitoring system in accordance with the present invention.

In FIG. 1, the motion of a patient 10 is transmitted to a sensing sheet 12 by direct physical contact, such as exists when the sensing sheet 12 is placed on a bed and the patient 10 lies on top of the sensing sheet 12. The sensing sheet 12 includes a number of spaced-apart sensing elements or transducers (not shown in FIG. 1) capable of converting applied forces into an electrical signals representative of the forces. One example of such a sensing sheet 12, described in detail below, employs sensing elements that function as variable capacitors whose capacitance changes in response to applied forces. Other types of sensing elements may also be employed, such as piezoelectric sensing elements, force-sensing resistors, etc.

The signals generated by the sensing sheet 12 are communicated to a nearby sensor signal processing unit (SSPU) 14. The unit 14 contains analog-to-digital (A/D) converters 16, a signal processor 18, and a radio-frequency (RF) modem 20. The A/D converters 16 continually translate the analog signals from the sensing sheet 12 into corresponding digital values. The signal processor 18 applies spatial weighting to the digital output streams from the A/D converters 16 to reflect the respective locations of the sensing elements on the sensing sheet 12, and uses the spatially-weighted digital signal streams in performing one or more analysis processes. Spatial weighting is described further below.

In general, the processor 18 monitors the outputs of the sensing elements to detect the occurrence of certain predetermined "patient states" that pertain to a particular analysis being performed. Generally, the patient states are defined by one or more thresholds associated with certain analysis variables. For example, an analysis process for determining whether the patient 10 is present may simply integrate the force distribution over the sensing sheet 12, as reported by the various sensing elements, and compare the integrated value with a predetermined threshold representing the minimum value that would be expected if a patient were present. Appropriate values to use for the threshold can be determined analytically or empirically. There may be a selectable threshold based on certain parameters, such as the patient's weight.

Much more sophisticated analysis processes can also be performed. Analyses may also include time as a parameter. For example, an analysis process may be used to help reduce the incidence of bedsores, which can develop if a patient remains in a given position too long. The movement of the center of the patient's mass over time can be monitored, and appropriate action taken when the extent of movement is less than a predetermined threshold for more than a predetermined time. Processes may be employed for detecting and providing information about patient agitation, respiration, reaction to drugs, sleep disorders, or seizures. The system can also be used to enhance patient safety and security. By monitoring weight changes on a patient's bed, the system can provide an indication that a patient has gotten up, or that an additional person is on the bed.

When significant patient states or state transitions are detected by the processor 18, a corresponding information message is generated by the processor 18 and transmitted on a wireless communications link 22 via the RF modem 20. In general, the information message contains information identifying the patient, such as the patient's name, room number, etc., and information about the detected patient state. In addition, the processor 18 may also update a local data collection log (not shown) maintained for administrative or diagnostic purposes.

In the illustrated system, it is desirable that the RF modem function as a "slave" with respect to a "master" modem 24 residing in a central information-processing unit (CIPU) 26. Because the CIPU 26 communicates with a number of SSPUs 14, it would be inefficient to continually maintain individual communications links 22 between the CIPU 26 and each SSPU 14. By employing a master-slave arrangement, a link 22 is in existence only when needed. When the slave modem 20 receives a message from the processor 18, it requests a connection with the master modem 24 using a separate, low-rate signaling channel (not shown). The master modem 24 informs the slave modem 20 when the link 22 has been established, whereupon the slave modem 20 transmits the information message. Preferably, the master modem 24 transmits a positive acknowledgement message to the slave modem 20 if the information message is received correctly.

It may be desirable that the master modem 24 also be capable of initiating the establishment of the link 22. This capability can be useful, for example, when configuration information, updates, or other information is to be transferred from the CIPU 26 to the SSPU 14. When directed by the master modem 24, the slave modem 20 monitors the link 22 for incoming messages containing such information and forwards these messages to the processor 18. Software executing in the processor 18 responds in a desired predetermined fashion.

When a patient state information message is received at the CIPU 26, the data is used to update a central database archive 30 and is also provided to a user interface platform 32. The information in the database archive 30 can be used for a variety of generally offline activities, such as administrative record keeping, statistics gathering, etc. The user interface platform 32 provides the information to one or more real-time users, who in general are medical personnel responsible for the care of the patient 10. For example, the platform 32 may include a graphical display at a nurses' desk to provide the information to a desk nurse 34. The platform 32 may also include paging equipment programmed to send an alert message to a floor nurse 36 or other personnel. The alert message preferably includes patient identifying information, such as the identity and room number of the patient 10, and a brief description of the detected patient state. For example, when a "patient not present" state is detected, an alert message such as "Jones, 302, Out Of Bed" may be generated.

As shown, the CIPU 26 may also communicate with other entities via a local- or wide-area network. There may be inter-departmental communications with other departments 38 of a medical facility, such communications typically occurring over a local-area network. Examples include communications with medical laboratories and administrative offices such as a patient billing department. There may also be wider-area communications with remote entities 40, such as a patient's family, affiliated research facilities, physicians' offices, and insurance companies, for example.

As a scaled-back alternative to the system of FIG. 1, the SSPU 14 may itself include a pager (not shown) in place of the slave RF modem 20, and the CIPU 26 and its network connections dispensed with. In such a system, the SSPU 14 itself sends a paging signal to the desk nurse 34, floor nurse 36, or other personnel as appropriate. While such a system has overall less functionality than the system of FIG. 1, it retains the important core functions of the sensing sheet 12 and SSPU 14, and can provide greater cost effectiveness and flexibility in deployment. Of course, other system configurations are also possible.

Figure 2:
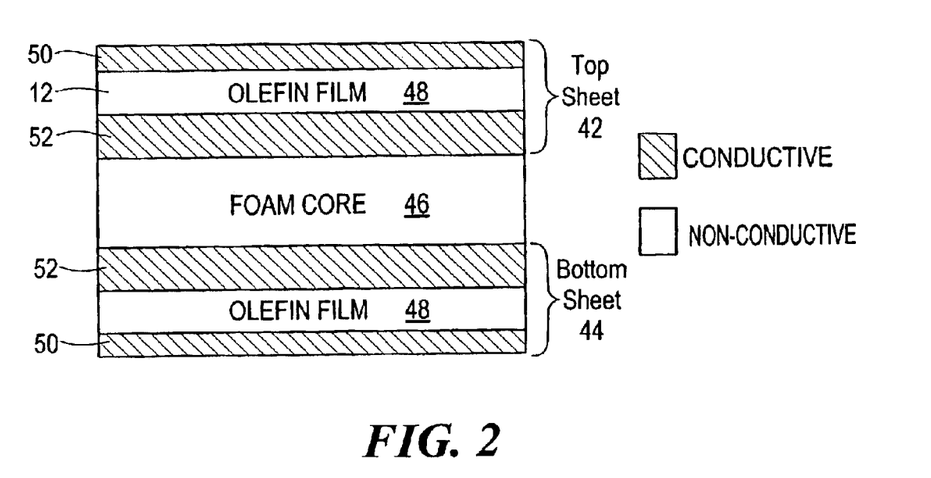
FIG. 2 is a diagram showing the arrangement of a multi-layer sensing sheet used in the system of FIG. 1.

As shown in FIG. 2, the sensing sheet 12 includes a number of layers laminated together. The sheet 12 includes a multi-layer top sheet 42, a multi-layer bottom sheet 44, and a foam core 46 disposed therebetween. Both the top sheet 42 and bottom sheet 44 include a layer of olefin film 48 approximately 0.0065" thick, such as sold by duPont, Inc. under the trademark TYVEK®. Both sides of each layer of film 48 are coated with conductive material. Each outer layer 50 is a ground plane covering substantially the entire surface of the respective film 48 to provide shielding from electrical noise. Each inner layer 52 has patterned conductive traces that define the sensing elements, as described in more detail below.

The conductive layers 50 and 52 are preferably made using conductive inks that are applied to the respective surfaces of the films 48 during manufacture of the sensing sheet 12. These layers are approximately 0.001" thick. The inner layers 52 are preferably made using a silver-based conductive ink for its excellent electrical properties. The outer layers 50 may be made using a copper-based conductive ink, which will have suitable electrical properties and lower cost than a silver-based ink.

The foam core 46 is approximately 0.5" thick when uncompressed. The compression properties of the foam core 46 can vary depending on the application, more specifically on the range of weights of the patient 10 being monitored. The compression properties of the foam core 46 largely dictate the sensitivity of the sensors, which refers to the change in sensor capacitance due to changes in applied force. For adults in a normal weight range, it is desirable that the foam core 46 deflect about 25% when a pressure of 25 lbs. per square foot is applied. The useful upper limit of deflection is approximately 50% of uncompressed thickness. If the sensing sheet 12 is to be used with a different class of patients 10, such as infants for example, it may be desirable to use a foam core 46 having different compression characteristics so as to achieve optimal sensitivity.

Figure 3:
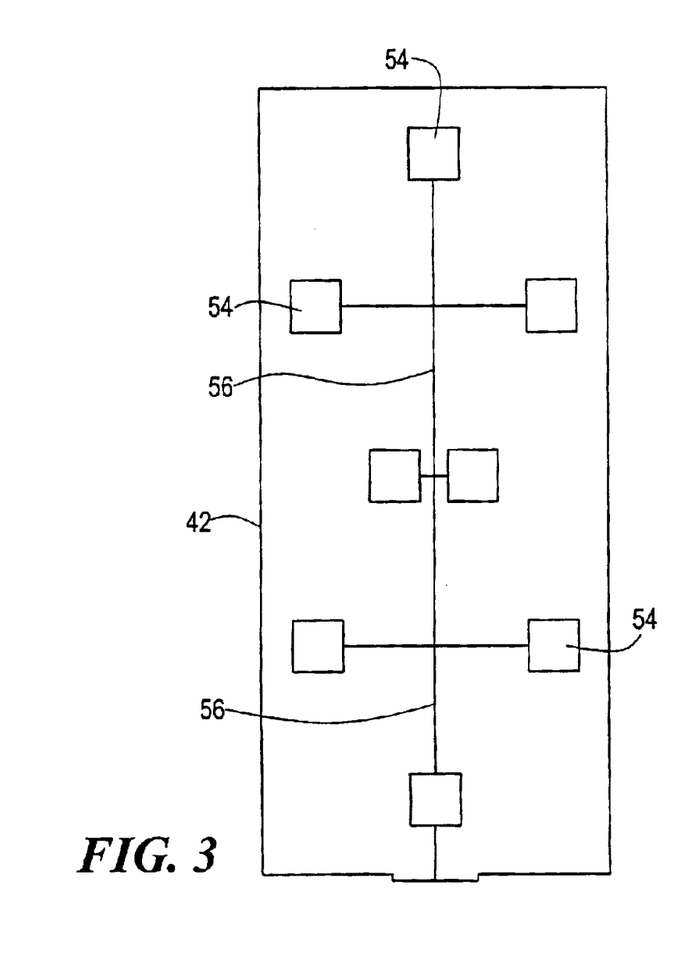
FIG. 3 is a layout diagram of a top layer of the sensing sheet of FIG. 2.

FIG. 3 shows the top sheet 42, specifically the surface on which the conductive layer 52 (FIG. 2) is formed. The top sheet 42 measures approximately 6.5 feet long by 3 feet wide. The conductive layer 52 comprises a number of conductive planar elements referred to as "plates" 54 interconnected by a conductive trace 56. A segment 58 of the trace 56 is formed at the bottom of the sheet 42 for purposes of establishing an electrical interconnection between the trace 56 and a separate connector (not shown), as described in more detail below. The plates 54 measure approximately 5" on a side.

Figure 4:
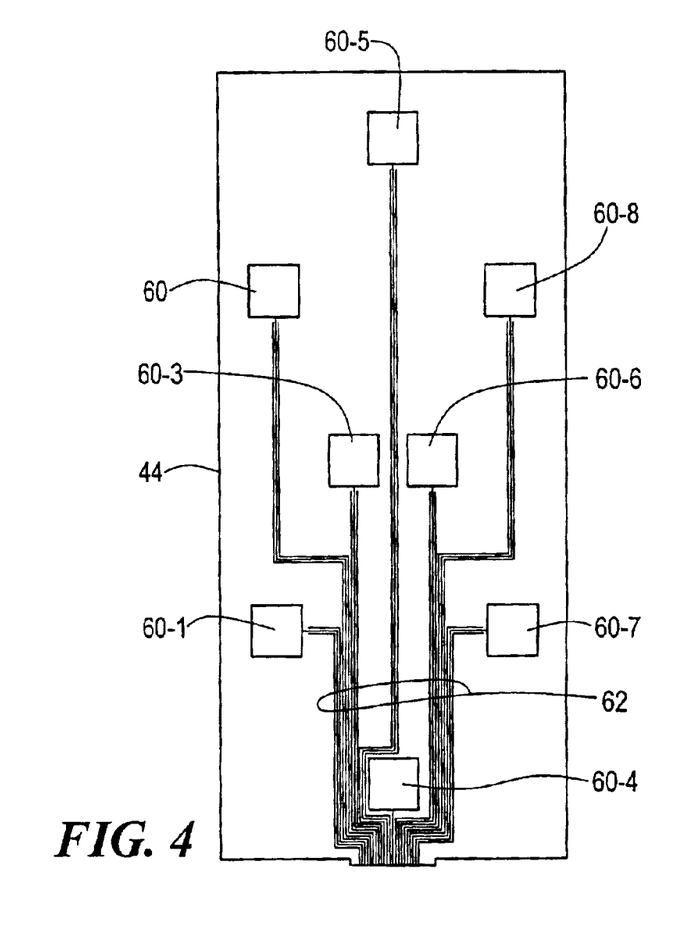
FIG. 4 is a layout diagram of a bottom layer of the sensing sheet of FIG. 2.

FIG. 4 shows the bottom sheet 44, specifically the surface on which the conductive layer 52 is formed. The bottom sheet 44 also measures 6.5 feet by 3 feet. Conductive plates 60 (shown as 60-1 through 60-8) are formed at respective positions corresponding to the positions of the plates 54 on the top sheet 42 (FIG. 3), so as to form eight plate capacitors when the sensing sheet 12 is assembled. The plates 60 are connected to respective traces in a set 62 that extends to the bottom edge of the bottom sheet 44. The traces 62 are described in more detail below.

In operation, a suitable drive signal such as a 5 volt peak-to-peak sine wave of 50 KHz is applied to the plates 54 of the top sheet 42 via the trace 56 formed thereon. This signal is capacitively coupled to each of the plates 60 of the bottom sheet 44. The capacitance of each plate capacitor formed by a given plate 54 and its opposite plate 60 changes in response to locally experienced forces that change the plate spacing by compressing the foam core 46 (FIG. 2). As a result, the respective strengths of the 50 KHz signals appearing on the plates 60 vary accordingly, and these signals are sampled and processed by the SSPU 14 (FIG. 1) as described above. In particular, different two-dimensional weights are applied to the signals from the plates 60 to reflect their respective spatial characteristics, including location, size, and shape. These spatial weights are chosen from a suitable two-dimensional space, such as a rectangular grid with vertices at (0, 0), (0, 1), (1, 0) and (1, 1). For the sheet 12 as shown herein, the plates 60 are of uniform size and are distributed symmetrically on the surface of the bottom layer 44. In this case, the spatial weights in the following table might be used, where each spatial weight corresponds to a different plate 60 as shown:

| Plate | X | Y |
| --- | --- | --- |
| 60-1 | 0.2 | 0.3 |
| 60-2 | 0.2 | 0.7 |
| 60-3 | 0.4 | 0.5 |
| 60-4 | 0.5 | 0.1 |
| 60-5 | 0.5 | 0.9 |
| 60-6 | 0.6 | 0.5 |
| 60-7 | 0.8 | 0.3 |
| 60-8 | 0.8 | 0.7 |

Figure 5:
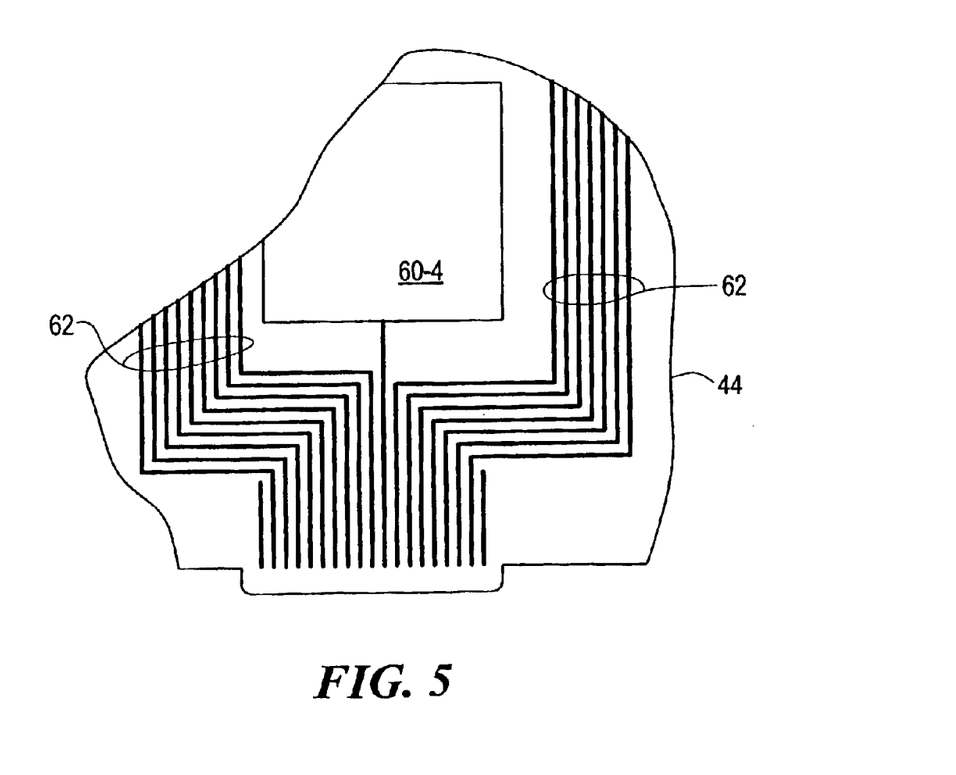
FIG. 5 is a first detailed layout view of a connection edge of the bottom layer of FIG. 4.

FIG. 5 shows the bottom edge of the bottom sheet 44 in more detail. The traces 62 are arranged in two groups, one to the right of the bottom-most plate 60 and the other to the left. The right group includes seven individual traces, consisting of four ground traces interspersed with three signal traces, one for each of the three plates 60 on the right side of the sheet 44 (FIG. 4). Similarly, the left group includes nine individual traces, consisting of five ground traces interspersed with four signal traces, one for the top-most plate 60 and one for each of the three plates 60 on the left side of the sheet 44 (FIG. 4).

Figure 6:
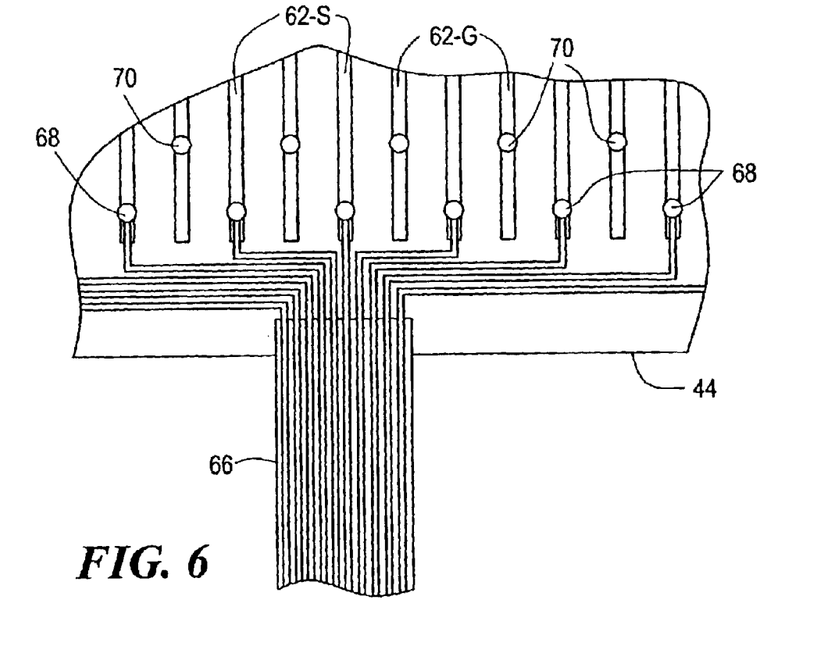
FIG. 6 is a second detailed layout view of the connection edge of the bottom layer of FIG. 4.

FIG. 6 shows the manner in which connections are formed between the traces 62 and a cable 66 at the connection edge of the bottom sheet 44. The traces 62 are shown as signal traces 62-S and ground traces 62-G. Each conductor of the cable 66 is provided with a solderless terminal 68 which is secured to the sheet 44 in contact with a corresponding signal trace 62-S. A conductive snap 70 is used to electrically couple each ground trace 62-G to the ground plane on the opposite surface of the sheet. Specifically, a male component (not shown) of the snap 70 extends through a hole in the trace 62-G and sheet 44, and the male component is received by a female component (not shown) on the other side. Although it is not shown in the Figures, it is generally desirable to place several such snaps 70 along the length of each ground trace 62-G, to minimize stray impedance in the ground path that can contribute to noise. Also, it may be desirable that the snaps 70 and/or terminals 68 be epoxied to the sheet 44 for an even more secure attachment.

Figure 7:
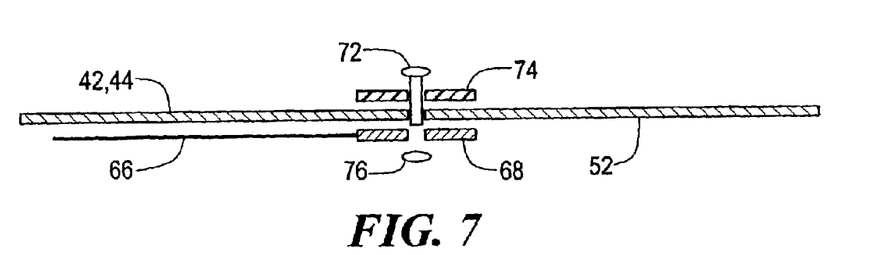
FIG. 7 is a detailed view of the connection between a cable lead and the top layer of FIG. 3 or the bottom layer of FIG. 4.

FIG. 7 shows the attachment of a conductive lead of the cable 66 to either sheet 42 or 44 in greater detail. A plastic rivet 72 extends through a copper washer 74, the sheet 42 or 44, and the solderless terminal 68 as shown. A rivet head 76 is placed over the rivet 72, and the rivet 72 and rivet head 76 are then squeezed together in a conventional fashion. By this action, the terminal 68 makes secure connection to the conductive layer 52 of the sheet 42, 44.

Figure 8:
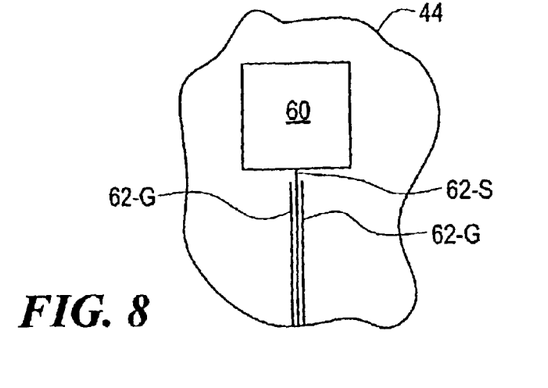
FIG. 8 is a detailed layout view of an area of the bottom layer of FIG. 4 in which a capacitor plate is formed.

FIG. 8 shows the area around a typical plate 60. The plate 60 is connected to a corresponding signal trace 62-S, which is surrounded on both sides by ground traces 62-G for shielding purposes. Each pair of ground traces 62-G extends alongside the entire run of the corresponding signal trace 62-S from plate 60 to the bottom edge of the sheet 44.

Figure 9A:
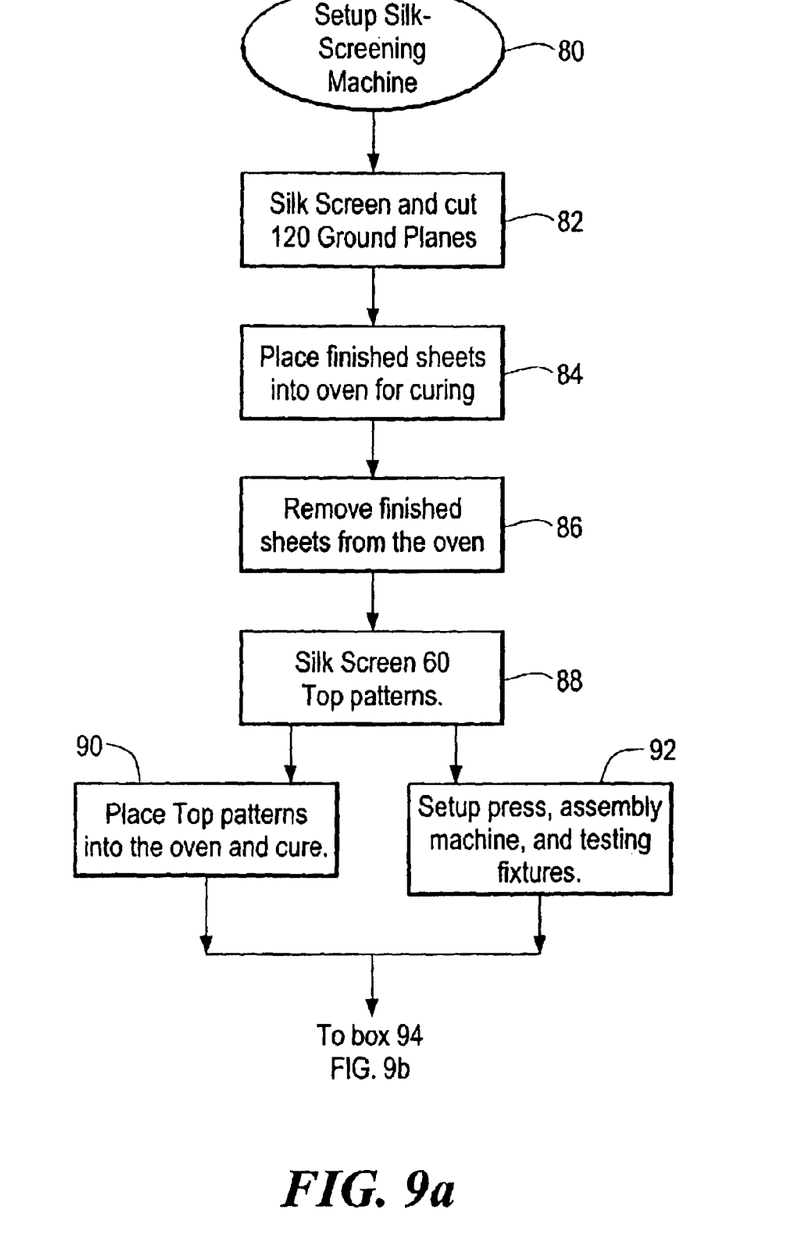
Figure 9B:
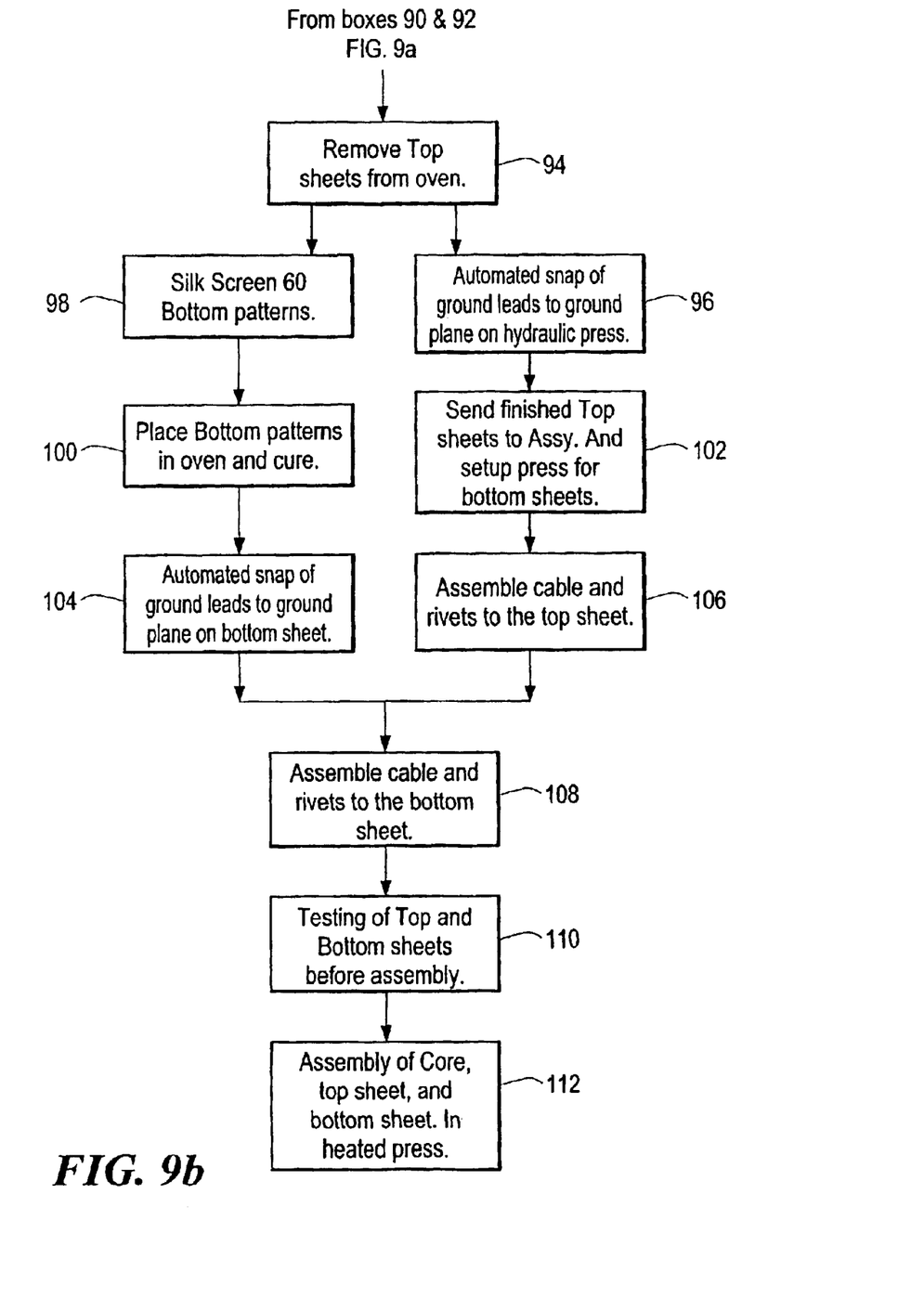

FIG. 9 shows a single-station process for manufacturing the sensing sheet 12. In step 80, a silk screening machine is set up with a roll of olefin film. At step 82, the outer conductive layer 50 (FIG. 2) is silk screened onto a length of film sufficient for 60 top sheets 42 and 60 bottom sheets 44. Because the outer layer 50 is a ground plane extending across the entire surface of each sheet, this layer can be deposited as one continuous film along 780 feet (120×6.5) of the olefin film. After the layer 50 has been deposited, the individual sheets are cut as each 6.5' length of film exits the machine.

At step 84, the sheets are placed into an oven to allow the conductive ink to dry. The sheets are then removed from the oven at step 86. At step 88, the patterned conductive layer 52 is silk screened onto the 60 top sheets 42, and these are returned to the oven for curing at step 90. At the same time, at step 92 a press, assembly machine and testing apparatus can be set up in preparation for the final assembly and testing of the sheets 12.

At step 94, the cured top sheets 42 are removed from the oven, and at step 96 ground leads are "snapped" to the ground plane of the cured top sheets 42 using snaps as described above with reference to FIG. 6. At the same time, at step 98 the patterned layer 52 is silk screened onto the bottom sheets 44. The bottom sheets 44 are then placed in the oven for curing at step 100, while at step 102 the top sheets 42 are moved to an assembly area and the press is set up for the bottom sheets 44. At step 104, ground leads are snapped to the ground plane of the cured bottom sheets 44, while at the same time at step 106 a cable assembly is riveted to each top sheet 42. At step 108, a cable assembly is riveted to each bottom sheet 44.

At step 110, each sheet 42 and 44 is tested for continuity of connections, such as between each plate 60 and its associated trace 62 for example. Each sheet is also tested for the absence of any short circuits between the outer and inner layers 50 and 52, which could occur for example if the conductive ink were to bleed through the olefin film. This testing is preferably done prior to the attachment of the cables. Once the cables are attached, additional testing is performed to ensure proper connectivity between the conductors of the cable and the various conductive elements on the sheet.

Figure 10:
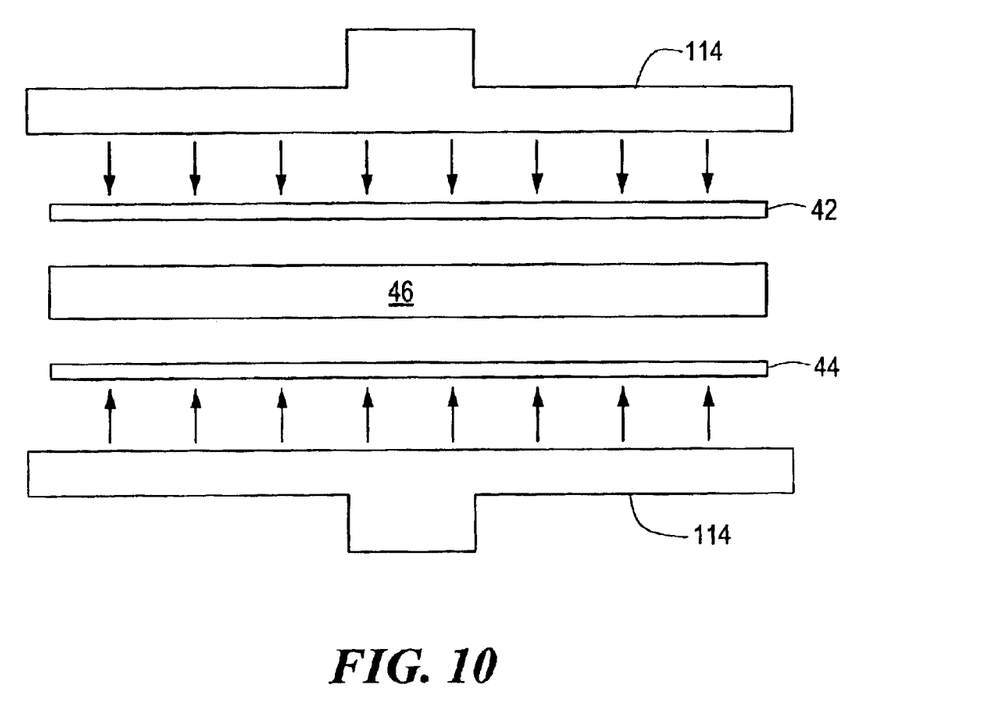
FIG. 10 is a diagram showing the manner in which heat pressing is used to laminate the layers of FIGS. 3 and 4 and additional layers to form the sensing sheet of FIG. 2.

At step 112 the top and bottom sheets 42 and 44 are assembled into the final sheet 12. The core 46 is pre-treated with a heat-activated adhesive on both surfaces, and then pressed together with the sheets 42 and 44 in a heated press. This process is illustrated in FIG. 10, where the elements 114 are heated press elements.

Figure 11A:
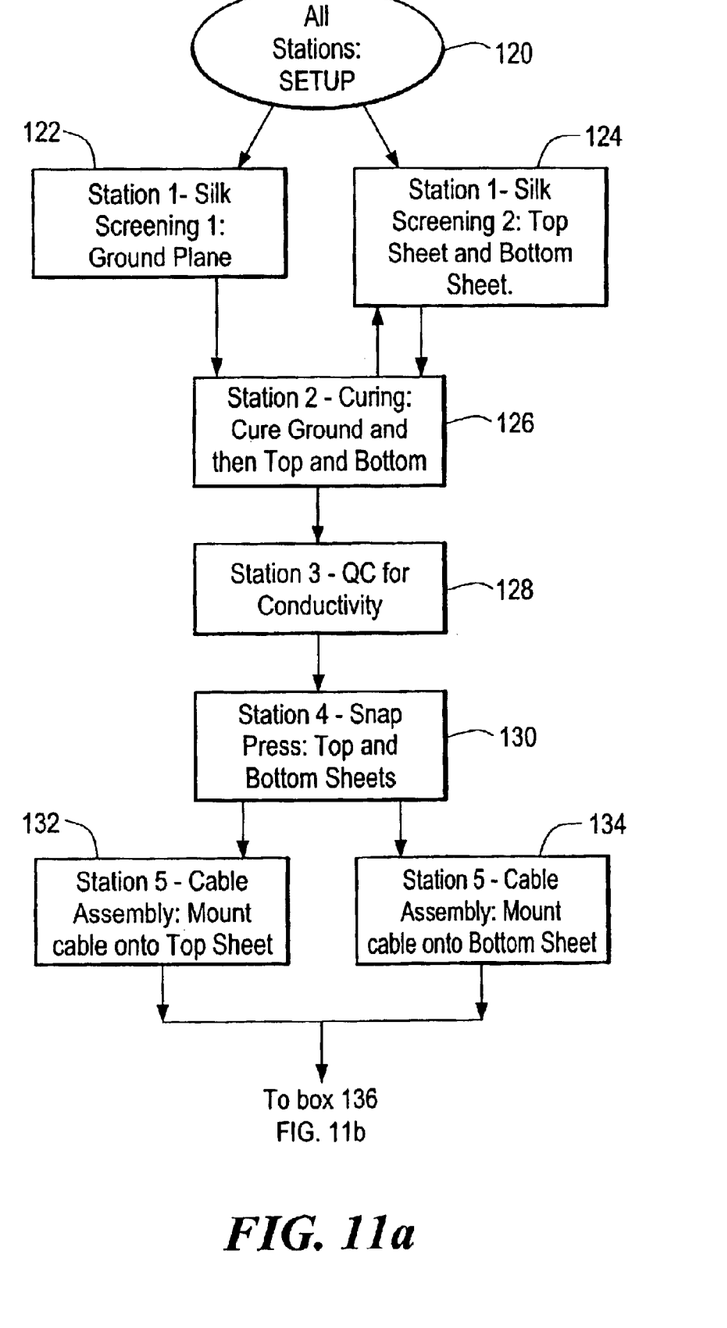
Figure 11B:
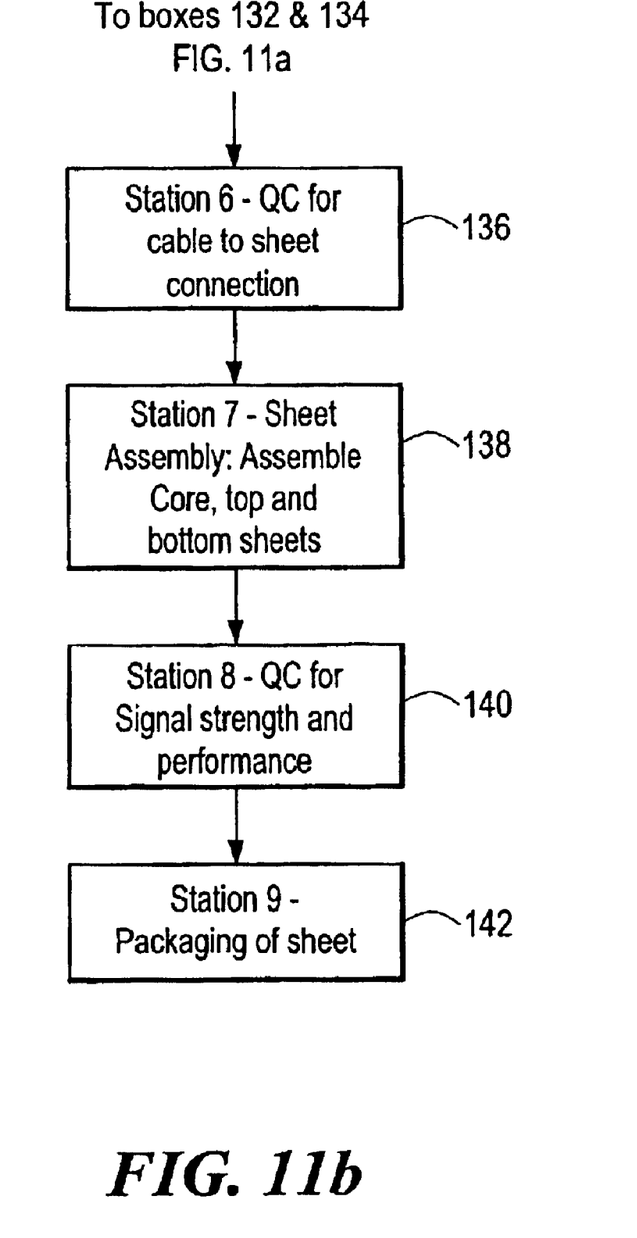

FIG. 11 illustrates a process for manufacturing the sensing sheet 12 which follows more of an assembly line model than the process of FIG. 9. It is assumed that there are separate workers at each station. Also, some of the equipment, such as the silk screening machines and cable assembly stations, are duplicated for improved throughput. The overall process reflected in steps 120–142 of FIG. 11 is generally the same as that shown in FIG. 9. However, much greater volumes of sheets 12 can be produced due to the assembly line structure. Several batches of material are in process simultaneously, with each batch being in a different stage of completion. The process of FIG. 11 is capable of yielding approximately 210 finished sensing sheets 12 per day, whereas the single-person process of FIG. 9 can yield approximately 60 sheets per day.

A patient monitoring system employing a laminar sensor sheet has been shown. It will be apparent to those skilled in the art that modifications to and variations of the disclosed methods and apparatus are possible without departing from the inventive concepts disclosed herein, and therefore the invention should not be viewed as limited except to the full scope and spirit of the appended claims.

What is claimed is:

1. A system for sensing status of a patient in a bed comprising:

a replaceable laminar sensor on said bed;

said laminar sensor having a plurality of force sensing elements distributed two-dimensionally throughout said sensor; and processing apparatus responsive to forces sensed by said sensor for forming a spatially weighted sum of the forces sensed by said sensor to provide a distribution of the forces throughout said laminar sensor, said processing apparatus providing an indication over time of a patient status in response to said weighted average.

2. The system of claim 1 wherein said laminar sensor comprises a sheet having discrete sensors therein.

3. The system of claim 2 wherein said discrete sensors include one of capacitive sensors, piezoelectric sensors, and resistive sensors.

4. The system of claim 1 wherein said laminar sensor further includes conductors extending from the discrete sensors to a connection point at an edge of said sheet.

5. The system of claim 2 wherein said sheet is dimensioned to cover said bed over a predetermined range of patient movement.

6. The system of claim 1 wherein said processing apparatus includes a near-bed processor and a central processor in communication with said near-bed processor through a communication link.

7. The system of claim 6 wherein said communication link is a wireless link having interfaces at said near-bed processor and said central processor.

8. The system of claim 1 wherein said processing apparatus provides patient status information including information regarding patient presence, patient position, patient agitation, patient seizures, patient respiration, and patient security.

9. The system of claim 1 wherein said processing apparatus provides patient status information relative to sleep disorders.

10. The system of claim 1 wherein said processing apparatus provides patient status information relative to patient drug reactions.

11. The system of claim 1 wherein said processing apparatus provides information relative to the presence or absence of patient activity sufficient to avoid bed sores.

12. The system of claim 1 further including a database for recording patient status.

13. The system of claim 12 wherein said processing apparatus provides adaptive indications of patient status in response to database information and sensor signals.

14. A sensing sheet for use in a patient monitoring system, the patient monitoring system including processing apparatus operative to calculate a spatially weighted sum of the respective values of sensor signals generated by the sensing sheet, the spatially weighted sum being calculated using a set of predetermined two-dimensional spatial weight values, the sensing sheet comprising:

a planar, flexible, electrically insulative substrate, the substrate having length and width substantially corresponding to the length and width of a patient's bed; and a pattern of sensing elements on the substrate, the sensing elements being spaced apart to define a two-dimensional sensing area on the patient's bed when the sensing sheet is placed thereon, the sensing elements having respective sizes, shapes and locations in relation to the predetermined two-dimensional spatial weight values such that the spatially weighted sum accurately reflects the spatial distribution of forces existing between a patient and the patient's bed when the sensing sheet is disposed therebetween.

15. A sensing sheet according to claim 14, wherein the substrate includes a set of laminated layers.

16. A sensing sheet according to claim 14, wherein the sensing elements comprise capacitors made from conductive planar elements disposed on the substrate.

17. A sensing sheet for use in a patient monitoring system, the patient monitoring system including processing apparatus operative to calculate a spatially weighted sum of the respective values of sensor signals generated by the sensing sheet, the spatially weighted sum being calculated using a set of predetermined two-dimensional spatial weight values, the sensing sheet comprising:

a first electrically insulative film, the first film having length and width substantially corresponding to the length and width of a patient's bed and having a pattern of conductive electrodes formed thereon, the conductive electrodes being spaced apart on the film to define a two-dimensional sensing area extending substantially entirely across the patient's bed when the sensing sheet is placed thereon, the conductive electrodes having respective sizes, shapes and locations in relation to the predetermined two-dimensional spatial weight values such that the spatially weighted sum accurately reflects the spatial distribution of forces existing between a patient and the patient's bed when the sensing sheet is disposed therebetween, the first film also including a set of conductive traces creating individual conductive paths from the electrodes to a connection area of the sensing sheet;

a second electrically insulative film laminated with the first film, the second film having length and width substantially the same as the length and width of the first film, the second film having a pattern of conductive electrodes formed thereon at respective locations directly opposite the respective locations of the electrodes on the first film, the second film also including conductive traces operative to electrically interconnect all of the conductive electrodes on the second film to each other and to the connection area of the sensing sheet; and a multi-conductor cable extending from the connection area of the sensing sheet and including a multi-terminal connector, the conductors of the cable being operative to create respective conductive paths from respective conductive traces of the first and second films to respective terminals of the multi-terminal connector.

18. A sensing sheet according to claim 17, wherein the signal traces are shielded by corresponding ground traces.

* * * * *